US009572535B2

(12) United States Patent
Shushan et al.

(10) Patent No.: US 9,572,535 B2
(45) Date of Patent: Feb. 21, 2017

(54) DYNAMIC MAPPING POINT FILTERING USING A PRE-ACQUIRED IMAGE

(71) Applicant: BIOSENSE WEBSTER (ISRAEL) LTD., Yokneam (IL)

(72) Inventors: Sharona Ben Shushan, Zichron Ya'acov (IL); Asaf Merschon, Karkur (IL); Fady Massarwa, Baka el Gharbiya (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 701 days.

(21) Appl. No.: 14/097,875

(22) Filed: Dec. 5, 2013

(65) Prior Publication Data
US 2015/0157267 A1 Jun. 11, 2015

(51) Int. Cl.
G06K 9/36 (2006.01)
A61B 5/00 (2006.01)
A61B 5/06 (2006.01)
G06T 17/20 (2006.01)
A61B 5/0402 (2006.01)
A61B 5/042 (2006.01)

(52) U.S. Cl.
CPC .......... *A61B 5/6869* (2013.01); *A61B 5/0084* (2013.01); *A61B 5/0402* (2013.01); *A61B 5/062* (2013.01); *A61B 5/6885* (2013.01); *G06T 17/20* (2013.01); *A61B 5/0044* (2013.01); *A61B 5/0073* (2013.01); *A61B 5/042* (2013.01); *A61B 5/7235* (2013.01); *G06T 2210/41* (2013.01)

(58) Field of Classification Search
USPC ..... 382/285, 128, 131, 115, 270; 250/208.1; 600/103, 409
See application file for complete search history.

(56) References Cited

U.S. PATENT DOCUMENTS 5,391,199 A 2/1995 Ben-Haim
5,443,489 A 8/1995 Ben-Haim
(Continued)

FOREIGN PATENT DOCUMENTS

EP 1 760 661 A2 3/2007
EP 1 837 828 A2 9/2007

OTHER PUBLICATIONS

EP Search Report, EP Application 14 196221.7 Dated Mar. 30, 2015.

*Primary Examiner* — Anh Do
(74) *Attorney, Agent, or Firm* — Notaro, Michalos & Zaccaria P.C.

(57) ABSTRACT

A method, including acquiring a body cavity image and receiving first and second sets of mapping points from a probe inserted into the cavity. A first registration, having a first cumulative error value, is performed between the first set's mapping points and the image, each of the first set's mapping points having a respective first point error value, and a 3D anatomical map is generated including the first set's mapping points whose respective first point error values are less than a specified threshold. A second registration is performed between the received mapping points and the image, each of the received mapping points having a respective second point error value, the second registration having a second cumulative error value lower than the first cumulative error value, and an updated 3D anatomical map is generated including the received mapping points whose respective second point error values are less than the specified threshold.

19 Claims, 5 Drawing Sheets

(56) References Cited

U.S. PATENT DOCUMENTS

| | | |
|---|---|---|
| 5,558,091 A | 9/1996 | Acker |
| 5,899,860 A | 5/1999 | Pfeiffer |
| 5,944,022 A | 8/1999 | Nardella |
| 5,983,126 A | 11/1999 | Wittkampf |
| 6,172,499 B1 | 1/2001 | Ashe |
| 6,177,792 B1 | 1/2001 | Govari |
| 6,456,864 B1 | 9/2002 | Swanson |
| 6,574,498 B1 | 6/2003 | Gilboa |
| 6,690,963 B2 | 2/2004 | Ben-Haim |
| 6,788,967 B2 | 9/2004 | Ben-Haim |
| 8,023,712 B2 * | 9/2011 | Ikuma ............... A61B 5/06 382/128 |
| 8,463,006 B2 * | 6/2013 | Prokoski ............ A61B 5/0064 382/128 |
| 8,494,227 B2 * | 7/2013 | Prokoski ............ A61B 5/0064 250/208.1 |
| 2007/0016007 A1 | 1/2007 | Govari |
| 2008/0221425 A1 | 9/2008 | Olson |
| 2009/0093806 A1 | 4/2009 | Govari |
| 2009/0138007 A1 | 5/2009 | Govari |

* cited by examiner

DYNAMIC MAPPING POINT FILTERING USING A PRE-ACQUIRED IMAGE

FIELD OF THE INVENTION

The present invention relates generally to medical imaging, and specifically to registering mapping points received from a medical probe to a pre-acquired three-dimensional image of a body cavity.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Patent Application 2007/0016007, to Govari et al., whose disclosure is incorporated herein by reference, describes a hybrid magnetic-based and impedance-based position sensing system. The system includes a probe adapted to be introduced into a body cavity of a subject.

U.S. Pat. No. 6,574,498, to Gilboa, whose disclosure is incorporated herein by reference, describes a system for determining the position of a work piece within a cavity of an opaque body. The system claims to use a transducer that interacts with a primary field, and several transducers that interact with a secondary field.

U.S. Pat. No. 5,899,860, to Pfeiffer, et al., whose disclosure is incorporated herein by reference, describes a system for determining the position of a catheter inside the body of a patient. A correction function is determined from the difference between calibration positions derived from received location signals and known, true calibration positions, whereupon catheter positions, derived from received position signals, are corrected in subsequent measurement stages according to the correction function.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention a method, including acquiring, from an imaging system, an image of a body cavity, receiving first and second sets of mapping points from a probe having a location sensor and inserted into the body cavity, performing, by a processor, a first registration between the mapping points in the first set and the image, each of the mapping points in the first set having a respective first point error value, the first registration having a first cumulative error value indicating a quality of the first registration, generating, using the first registration, a three-dimensional (3D) anatomical map including the mapping points in the first set whose respective first point error values are less than a point error threshold, performing a second registration between the mapping points in the first and the second sets and the image, each of the mapping points in the first and the second sets having a respective second point error value, the second registration having a second cumulative error value lower than the first cumulative error value, and generating an updated 3D anatomical map including the mapping points in the first and the second sets whose respective second point error values are less than the point error threshold.

In some embodiments, the 3D anatomical map and the updated 3D anatomical map may be presented on a display. In additional embodiments, the body cavity may include a heart, and wherein the probe may include an intracardiac catheter. In further embodiments, the 3D anatomical map may include an electroanatomical map.

In supplementary embodiments, the second registration is performed upon a specific time period elapsing after the first registration. In additional embodiments, the second registration is performed upon the second set having a specific number of mapping points. In further embodiments, the point error threshold may be specified prior to performing the first registration, an initial point error value is calculated for each of the mapping points in the second set.

In some embodiments, the first point error value for a given mapping point indicates a first quality of the given mapping point relative to the first registration, and the second point error value for the given mapping point indicates a second quality of the given mapping point relative to the second registration. In additional embodiments, prior to the second registration, a respective first point error value is calculated for each of the mapping points in the second set, and the mapping points in the second set whose respective first point error values are less than the point error threshold are included in the first map.

There is also provided, in accordance with an embodiment of the present invention an apparatus, including a probe, configured for insertion into a body cavity of a patient and having a location sensor for measuring a position of a distal end of the probe inside the body cavity, and a processor configured to acquire, from an imaging system, an image of the body cavity, to receive first and second sets of mapping points from the probe inserted into the body cavity, to perform a first registration between the mapping points in the first set and the image, each of the mapping points in the first set having a respective first point error value, the first registration having a first cumulative error value indicating a quality of the first registration, to generate, using the first registration, a three-dimensional (3D) anatomical map including the mapping points in the first set whose respective first point error values are less than a point error threshold, to perform a second registration between the mapping points in the first and the second sets and the image, each of the mapping points in the first and the second sets having a respective second point error value, the second registration having a second cumulative error value lower than the first cumulative error value, and to generate an updated 3D anatomical map including the mapping points in the first and the second sets whose respective second point error values are less than the point error threshold.

There is further provided, in accordance with an embodiment of the present invention a computer software product, operated in conjunction with a probe that is configured for insertion into a body cavity of a patient and includes a location sensor for measuring a location of a distal end of the probe inside the body cavity, the product including a non-transitory computer-readable medium, in which program instructions are stored, which instructions, when read by a computer, cause the computer to acquire, from an imaging system, an image of the body cavity, to receive first and second sets of mapping points from a probe inserted into the body cavity, to perform a first registration between the mapping points in the first set and the image, each of the mapping points in the first set having a respective first point error value, the first registration having a first cumulative error value indicating a quality of the first registration, to generate, using the first registration, a three-dimensional (3D) anatomical map including the mapping points in the first set whose respective first point error values are less than a point error threshold, to perform a second registration between the mapping points in the first and the second sets and the image, each of the mapping points in the first and the second sets having a respective second point error value, the second registration having a second cumulative error value lower than the first cumulative error value, and to generate an updated 3D anatomical map including the mapping points in the first and the second sets whose respective second point error values are less than the point error threshold.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Physiological or anatomical mapping procedures typically create a map comprising map points (also referred to herein as mapping points) collected from an electroanatomical mapping system. Each map point comprises a respective coordinate within a body cavity, and possibly a physiological property collected by a medical probe at the respective coordinate. While mapping a body cavity such as a chamber of a heart, the mapping points may be registered to a pre-acquired image of the body cavity, thereby providing practical visualization of the physiological properties that are being measured in the body cavity.

While collecting mapping points from a body cavity, embodiments of the present invention provide methods and systems for dynamically filtering some of the mapping points from a three-dimensional (3D) anatomical map that is based on a pre-acquired image. In some embodiments, upon receiving a first set of mapping points from the body cavity, an initial registration is performed between the mapping points in the first set and the pre-acquired image, a first cumulative error value is calculated that indicates a quality of the initial registration, and a three-dimensional (3D) anatomical map is created that includes the mapping points in the first set.

Subsequent to receiving the first set of mapping points a second set of mapping points can be collected from the body cavity, and a second registration is performed between the mapping points in the first and the second sets of mapping points and the pre-acquired image. Additionally, a point error value can be calculated for each of the mapping points in the first and the second sets, and a second cumulative error value can be calculated. Upon detecting that the second cumulative error value is less than the first cumulative error value, an updated 3D anatomical map can be generated that includes the mapping points in the first and the second sets whose respective point error values are less than a point error threshold.

In some embodiments, a 3D coloring algorithm can be used to assign different colors to different physiological property values of the body cavity, and systems implementing embodiments of the present invention can present the best possible alignment of the mapping points with the pre-acquired image by periodically selecting which of the received mapping points to include in the 3D anatomical map, and which of the received mapping points to exclude from the map.

System Description

Figure 1:
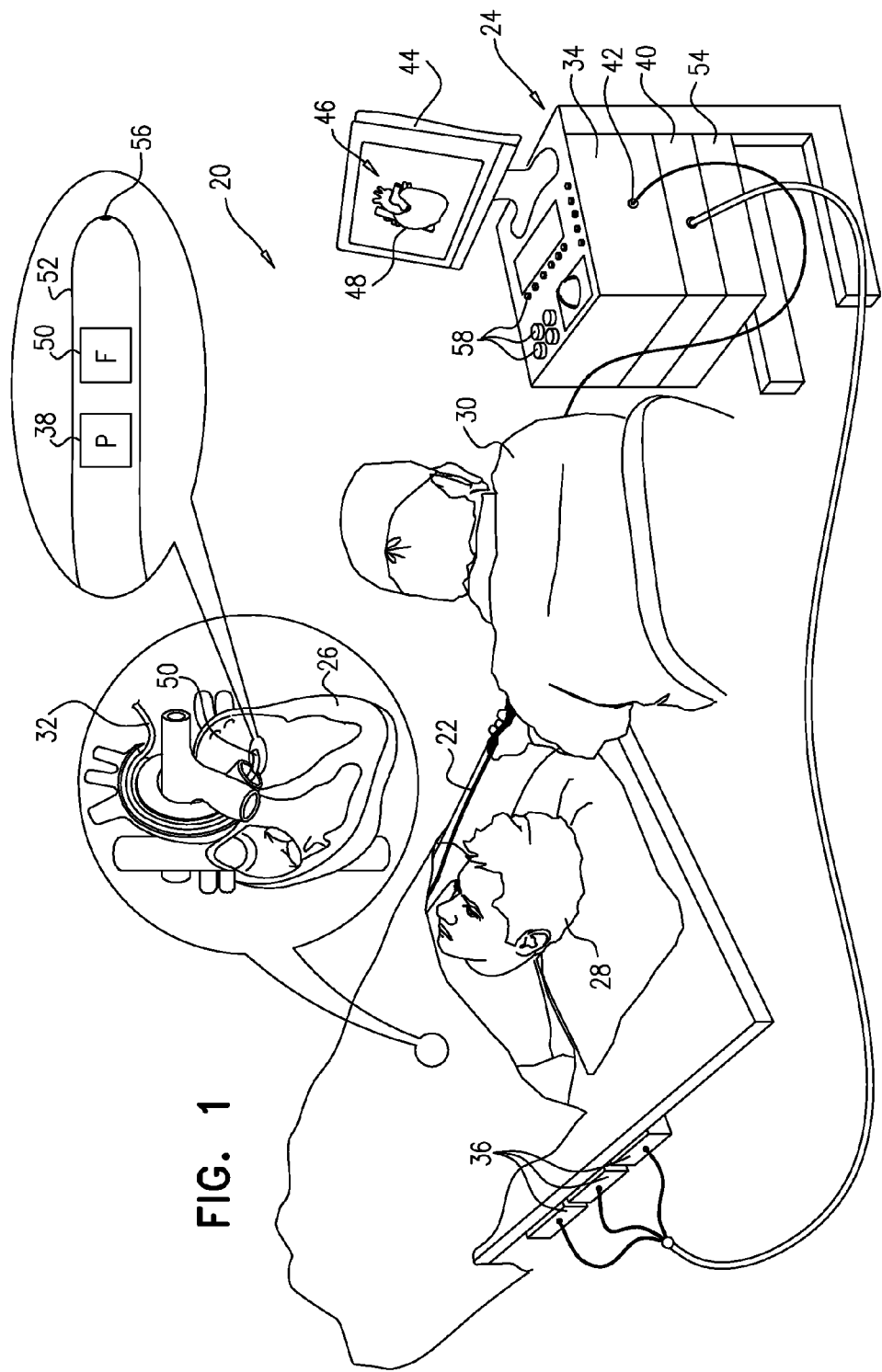
FIG. 1 is a schematic pictorial illustration of a medical system for mapping a cardiac chamber, in accordance with an embodiment of the present invention.

FIG. 1 is a schematic, pictorial illustration of an intracardiac mapping system 20, in accordance with an embodiment of the present invention. System 20 comprises a probe 22, such as an intracardiac catheter, and a control console 24. In embodiments described hereinbelow, it is assumed that probe 22 is used for diagnostic or therapeutic treatment, such as for mapping electrical potentials in a heart 26 of a patient 28. Alternatively, probe 22 may be used, mutatis mutandis, for other therapeutic and/or diagnostic purposes in the heart or in other body organs.

An operator 30 inserts probe 22 through the vascular system of patient 28 so that a distal end 32 of probe 22 enters a chamber of heart 26. Console 24 typically uses magnetic position sensing to determine position coordinates of distal end 32 inside heart 26. To determine the position coordinates, a driver circuit 34 in console 24 drives field generators 36 to generate magnetic fields within the body of patient 28. Typically, field generators 36 comprise coils, which are placed below the patient's torso at known positions external to patient 28. These coils generate magnetic fields in a predefined working volume that contains heart 26. A magnetic field sensor 38 (also referred to herein as location sensor 38) within distal end 32 of probe 22 generates electrical signals in response to these magnetic fields. A signal processor 40 processes these signals in order to determine the position coordinates of distal end 32, typically including both location and orientation coordinates. The method of position sensing described hereinabove is implemented in the CARTO™ mapping system produced by Biosense Webster Inc., of Diamond Bar, Calif., and is described in detail in the patents and the patent applications cited herein.

Location sensor 38 transmits a signal to console 24 that is indicative of the location coordinates of distal end 32.

Location sensor 38 may comprise one or more miniature coils, and typically comprises multiple coils oriented along different axes. Alternatively, location sensor 38 may comprise either another type of magnetic sensor, or position transducers of other types, such as impedance-based or ultrasonic location sensors. Although FIG. 1 shows a probe with a single location sensor, embodiments of the present invention may utilize probes with more than one location sensor.

In an alternative embodiment, the roles of location sensor 38 and magnetic field generators 36 may be reversed. In other words, driver circuit 34 may drive a magnetic field generator in distal end 32 to generate one or more magnetic fields. The coils in generator 36 may be configured to sense the fields and generate signals indicative of the amplitudes of the components of these magnetic fields. Processor 40 receives and processes these signals in order to determine the position coordinates of distal end 32 within heart 26.

Although in the present example system 20 measures the position of distal end 32 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

Processor 40 typically comprises a general-purpose computer, with suitable front end and interface circuits for receiving signals from probe 22 and controlling the other components of console 24. Processor 40 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 40 may be carried out by dedicated or programmable digital hardware components.

An input/output (I/O) interface 42 enables console 24 to interact with probe 22. Based on the signals received from probe 22 (via interface 42 and other components of system 20), processor 40 drives a display 44 to present operator 30 with an image 46 showing the position of distal end 32 in the patient's body, as well as status information and guidance regarding the procedure that is in progress.

Probe 22 also comprises a force sensor 50 contained within distal end 32. Force sensor 50 measures a force applied by a distal tip 52 of probe 22 to the endocardial tissue of heart 26 by generating a signal to the console that is indicative of the force exerted by the distal tip on the endocardial tissue. In one embodiment, the force sensor may comprise a magnetic field transmitter and receiver connected by a spring in distal end 32, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

Additionally or alternatively, system 20 may comprise an automated mechanism (not shown) for maneuvering and operating probe 22 within the body of patient 28. Such mechanisms are typically capable of controlling both the longitudinal motion (advance/retract) of probe 22 and transverse motion (deflection/steering) of distal end 32 of the probe. In such embodiments, processor 40 generates a control input for controlling the motion of probe 22 based on the signals provided by the magnetic field sensor in the probe.

In embodiments described herein, processor 40 is configured to collect image data from a medical imaging system (not shown) such as a magnetic resonance imaging (MRI) system, or a computed tomography (CT) system, or a probe mapping system such as the CARTO™ mapping system. As described hereinbelow, processor 40 uses the image data to construct a simulated surface of the cardiac chamber in question. In order to map the cardiac chamber in question, operator 30 advances probe 22 so that distal tip 52 engages endocardial tissue at multiple locations, and processor 40 "registers" the multiple locations on the simulated surface produced from the image data. Thus, the system collects multiple map points, with each map point comprising a coordinate on the inner chamber surface. In embodiments of the present invention, processor 40 can process signals received from force sensor 50 in order to detect when distal tip 52 is in contact with the endocardial tissue.

In alternative embodiments, probe 22 may comprise an electrode 56 coupled to the distal end and configured to function as an impedance-based position transducer. Additionally or alternatively, electrode 56 can be configured to measure a certain physiological property (e.g., the local surface electrical potential) at each of the multiple locations. In some embodiments, system 20 can correlate the position measurements and the electrical potential measurements. In other words, system 20 can collect multiple map points, with each map point comprising a coordinate on the inner chamber surface and a respective physiological property measurement at this coordinate.

During the diagnostic treatment, processor 40 presents image 46 of the simulated surface, with the registered location measurements laid thereon. In the present embodiment, the fusion of the simulated surface and the location measurements is referred to herein as a 3D anatomical map 48 (also referred to herein as map 48). In operation, after collecting the image data and the location measurements, processor 40 can construct map 48, store data representing the image and the 3D anatomical map in a memory 54, and present map 48 to operator 30 on display 44. To construct map 48, processor 40 can execute an algorithm such as the Fast Anatomical Mapping (FAM) algorithm that is described in U.S. Patent Application Publication 2011/0152684, whose disclosure is incorporated herein by reference.

Memory 54 may comprise any suitable volatile and/or non-volatile memory, such as random access memory or a hard disk drive. In some embodiments, operator 30 can manipulate map 48 using one or more input devices 58.

Although FIG. 1 shows a particular system configuration, other system configurations can also be employed to implement embodiments of the present invention, and are thus considered to be within the spirit and scope of the present invention. For example, the methods described hereinbelow may be applied using position transducers of types other than the magnetic field sensor described above, such as impedance-based or ultrasonic location sensors. The term "position transducer" as used herein refers to an element mounted on probe 22 which causes console 24 to receive signals indicative of the coordinates of the distal end. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in therapeutic and diagnostic applications using not only catheters, but also probes of other types, both in the heart and in other body organs and regions.

Simulated Surface Visualization

Figure 2:
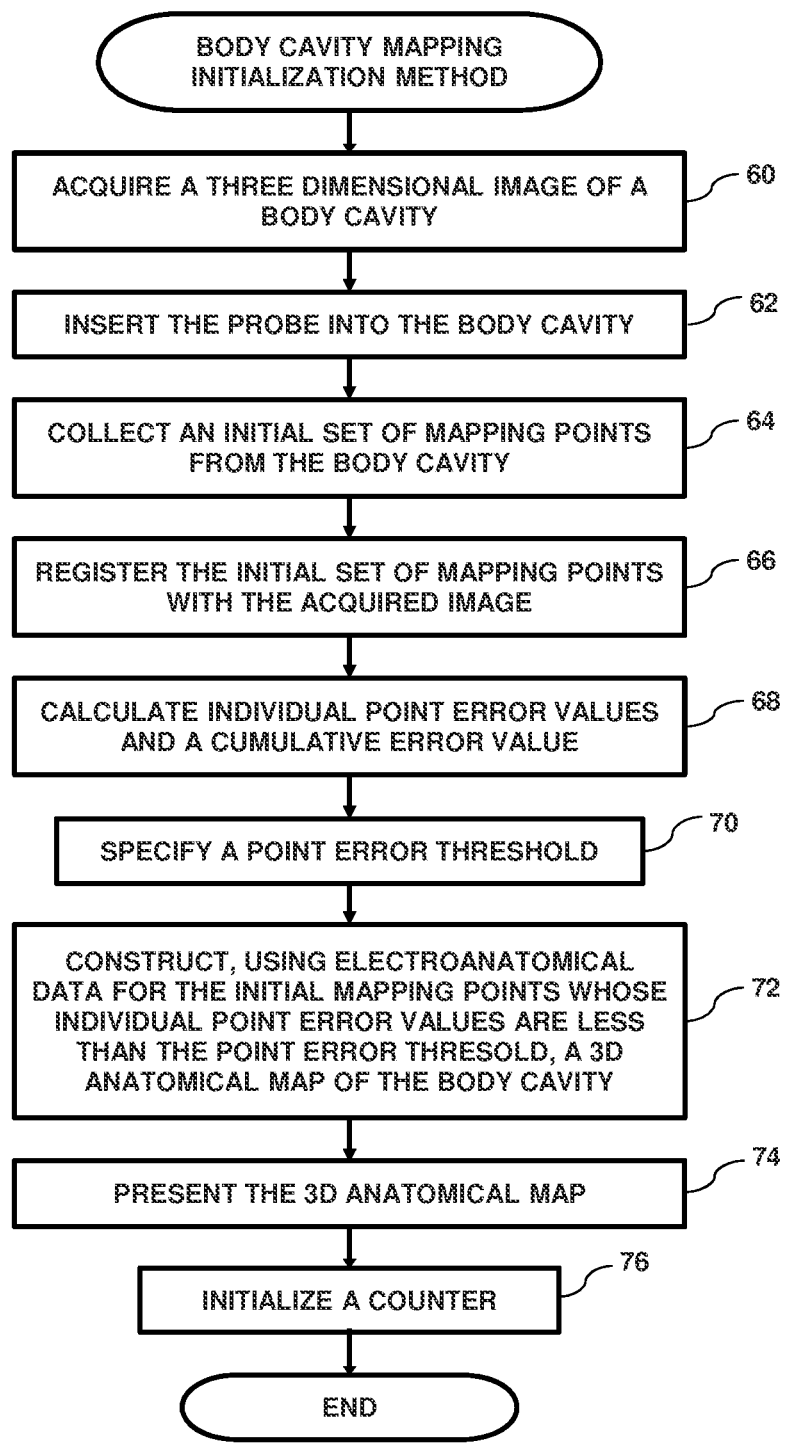
FIG. 2 is a flow diagram that schematically illustrates a method of initializing a map of the cardiac chamber, in accordance with an embodiment of the present invention.
Figure 3:
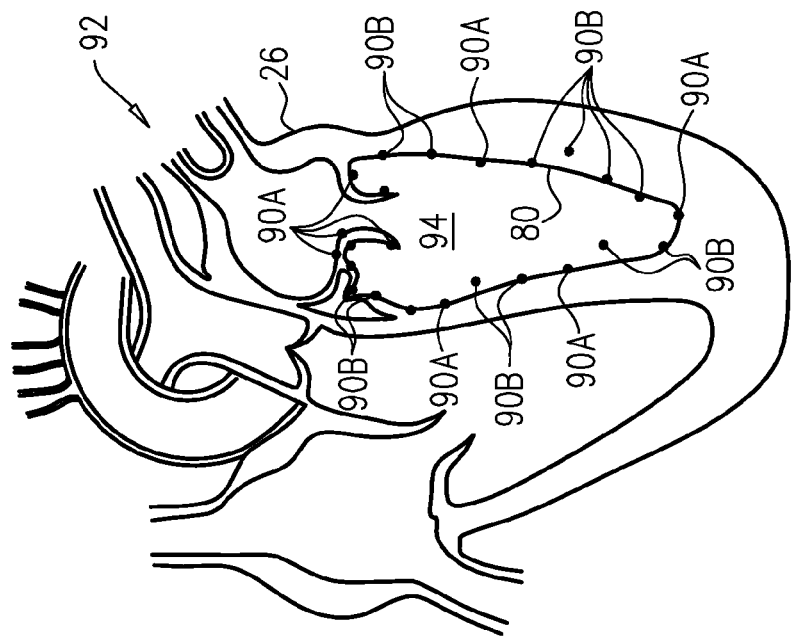
FIG. 3 is a schematic detail view showing a distal tip of a catheter in contact with endocardial tissue of the cardiac chamber, in accordance with an embodiment of the present invention.
Figure 4:
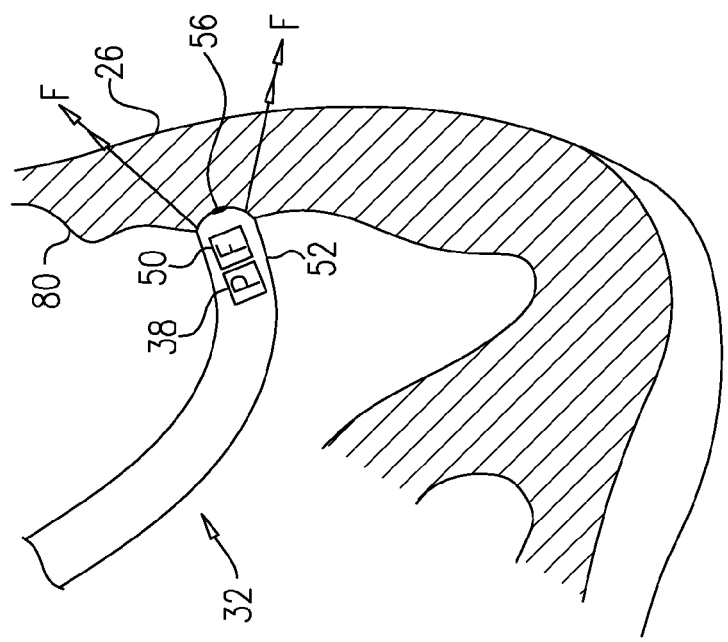
FIG. 4 is a schematic pictorial illustration of mapping points received from the distal tip in contact with the endocardial tissue.

FIG. 2 is a flow diagram that schematically illustrates a method of initializing map 48, FIG. 3 is a schematic detail view showing distal tip 52 in contact with endocardial tissue 80 of heart 26, and FIG. 4 is a schematic detail view of mapping points 90 collected by probe 22 and mapped to a pre-acquired image 92 (also referred to herein as image 92), in accordance with an embodiment of the present invention. Mapping points 90 can be differentiated by appending a letter to the identifying numeral, so that the mapping points comprise mapping points 90A and 90B.

In an acquire step 60, processor 40 acquires image 92 of heart 26. Examples of the pre-acquired images include, but are not limited to, three-dimensional images such as magnetic resonance imaging (MRI) images, magnetic resonance tomography (MRT) images and computed tomography (CT) images. For illustrative purposes, the image 92 shown in FIG. 4 comprises a two-dimensional "slice" of the three-dimensional pre-acquired image that is acquired in step 60.

In an insertion step 62, operator 30 inserts probe 22 into a chamber of heart 26 (also referred to herein as the cardiac chamber), and advances the probe so that distal tip 52 engages endocardial tissue 80 and exerts force F on the endocardial tissue, as shown in FIG. 3. To verify contact between distal tip 52 and endocardial tissue, processor 40 receives force measurements from force sensor 50 that indicate force F.

In a collection step 64, processor 40 collects initial mapping points 90A from probe 22. In addition to mapping points 90A, FIG. 4 shows additional mapping points 90B that processor 40 collects at a subsequent time, as described in the text referencing FIG. 6 hereinbelow. In embodiments herein, all mapping points 90A may also be referred to as a first set of mapping points 90, and all mapping points 90B may also be referred to as a second set of mapping points 90.

To collect each mapping point 90, operator 30 maneuvers probe 22 so that distal tip 52 presses against a given point of endocardial tissue 80, and upon receiving a signal from force sensor 50 indicating that distal tip 52 is pressing against the endocardial tissue, processor 40 automatically acquires location measurements from location sensor 38 indicating a current position of distal end 32. In the example shown in FIG. 4, the distal tip of probe 22 is collecting mapping points 90 from a left ventricle 94 of heart 26. In some embodiments, the mapping points may also comprise electroanatomical data such as local activation times.

In embodiments where processor 40 receives the location measurements from magnetic field sensor 38, the processor can map the received magnetic field measurements to corresponding locations on the simulated surface. In embodiments where processor 40 receives the location measurements from electrode 56, the location measurements comprising impedances to a current transmitted through the electrode, the processor can map the received impedance measurements to corresponding locations on the simulated surface.

In a registration step 66, processor 40 performs an initial registration by registering mapping points 90A with image 92. In some embodiments, processor 40 can register mapping points 90A with image 92 by performing a surface alignment of the collected mapping points to the pre-acquired image.

In a calculation step 68, processor 40 calculates an initial point error value for each mapping point 90A, and calculates a cumulative error value for the registration performed in step 66. Each of the initial point error values indicates a quality of its respective mapping point relative to the registration performed in step 66, and the cumulative point error value indicates an overall quality of the registration. To calculate the initial point error value measuring a quality of a given mapping point 90, processor 40 can calculate a distance of the given mapping point from image 92, calculate a distance of the given mapping point from surface 104, or an average (possibly weighted) of the two.

To calculate the cumulative error for the registration, processor 40 can calculate a set of functions AF1 ... AFn, where each function has a respective weight K1 ... Kn, so that the sum of all the respective weights is 1, and the cumulative error is $$AF1*K1+AF2*K2 \ldots +AFn*Kn \tag{1}$$

Examples of weighting functions that processor 40 can use to calculate the cumulative error value include, but are not limited to:

An average of the point error values.

A standard deviation of the point error values.

A total sum of volumes occupied by only one of the models used to represent heart 26. For example, processor 40 can identify 3D image regions that are present in pre-acquired image 92 but are not present in 3D anatomical map 48, and sum the volumes of the identified 3D image regions. Alternatively, processor 40 can identify 3D mapping regions that are present in 3D anatomical map 48 but are not present in pre-acquired image 92, and sum the volumes of the identified 3D mapping regions.

In operation, the functions and their respective weights can be changed according to the type of image 92 that is acquired in step 60 (e.g., an MRI image, an MRT image or a CT image, as described supra). Additionally or alternatively, the functions and their respective weights can be either pre-configured, automatic, user controlled or any combination of the aforementioned options.

In a specify step 70, processor 40 specifies a point error threshold, and the method ends. As explained hereinbelow, processor 40 uses the point error threshold to determine whether or not to include a given mapping point 90 in 3D anatomical map 48. The point error threshold can be hard-coded or dependent on a calculation such as a percentage of the cumulative error value calculated in step 68 or the lowest initial point error value which is below the median of the initial point error values. Alternatively, the point error threshold may be configurable by the operator.

In a construction step 72, using the mapping points collected in step 64 whose individual point error values are less than the point error threshold, processor 40 constructs map 48, and presents the map on display 44 in a presentation step 74.

Figure 5B:
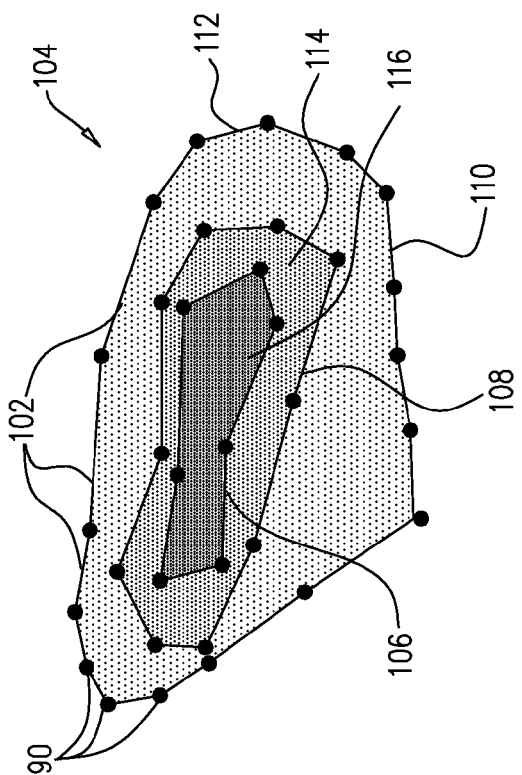
FIGS. 5A and 5B are schematic pictorial illustrations showing stages of creating the map of the cardiac chamber.
Figure 5A:
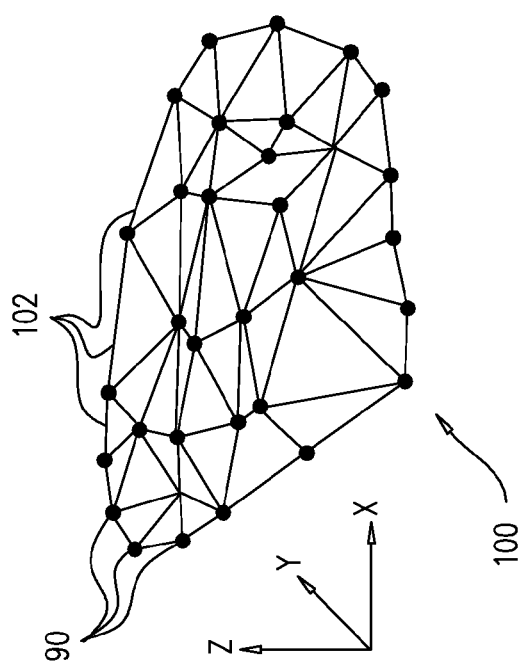

FIGS. 5A and 5B are diagrams illustrating stages in using mapping points 90 (i.e., either mapping points 90A or mapping points 90A and 90B) to construct map 48, in accordance with an embodiment of the invention. In a first stage, as shown in FIG. 5A, processor 40 connects mapping points 90 to define a mesh 100 of line segments 102. Mesh 100 typically, although not necessarily, is a triangular mesh. In some embodiments, the processor 40 uses a Ball-Pivoting Algorithm (BPA) to produce mesh 100. In alternative embodiments, processor 40 can generate mesh 100 as a Delaunay triangulation, comprising a plurality of triangles having vertices corresponding to mapping points 90. The triangles of the triangulation may be based on Voronoi diagrams formed about the mapping points. Apart from, or in addition to, the BPA and the Delaunay triangulation described hereinabove, processor 40 may use any convenient method that is known in the art for forming mesh 100.

In a second stage, as shown in FIG. 5B, processor 40 generates a generally smooth surface 104 connecting mapping points 90 and line segments 102. To generate surface 104, processor 40 typically uses interpolation and/or extrapolation. Additionally, to ensure that surface 104 is generally smooth, processor 40 may adjust the surface so as to be close to, but not necessarily include, some of mapping points 90 and line segments 102.

In the example shown in FIG. 5B, surface 104 has contours 106, 108 and 110. In embodiments of the present invention, map 48 may comprise an electroanatomical map showing electroanatomical data such as local activation times of various regions of heart 26. In additional embodiments, processor 40 can use a coloring algorithm to present the activation times as different color shadings, wherein a given color shading corresponds to a single activation time or a range of activation times. In the example shown in FIG. 5B, the color shadings are presented as fill patterns 112, 114 and 116.

Finally, in an initialization step 76, processor 40 initializes a counter. As explained hereinbelow in the flow diagram described in FIG. 6, the counter can be used to track a number of mapping points 90 received since the most recent registration of mapping points 90 to image 92, or a time elapsed since the most recent registration.

Figure 6:
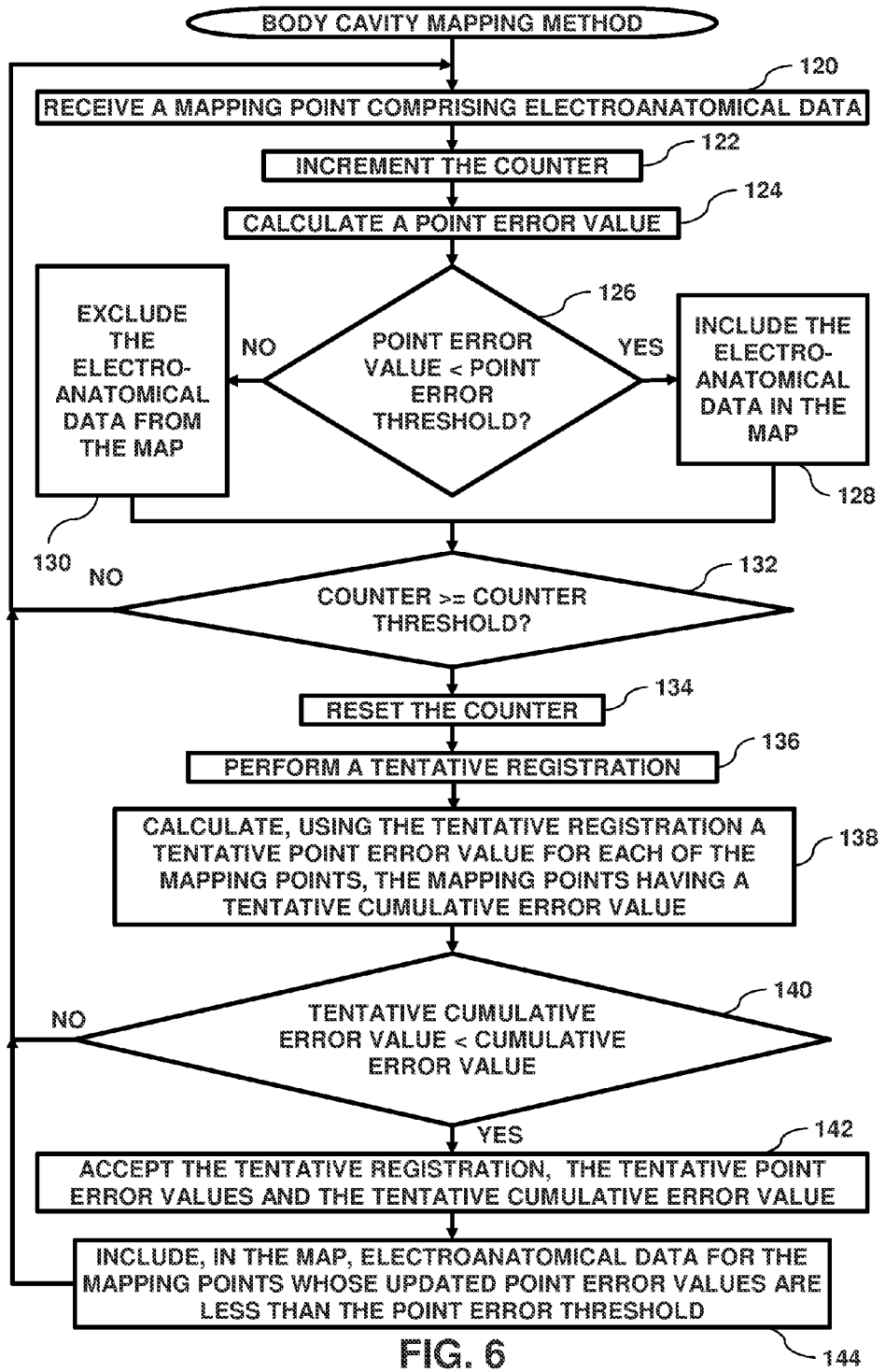
FIG. 6 is a flow diagram that schematically illustrates a method of constructing the map of the cardiac chamber upon receiving additional mapping points from the distal tip, in accordance with an embodiment of the present invention.

FIG. 6 is a flow diagram that schematically illustrates a method of updating map 48 upon receiving additional mapping points 90B, in accordance with an embodiment of the present invention. Prior to executing the steps of the flow diagram shown in FIG. 6, the counter, the cumulative error value and the registration have initial values, as described in the text referencing FIG. 2 hereinabove. Additionally, while the flow diagrams shown in FIGS. 2 and 6 describe mapping electroanatomical data, mapping other types of data is considered to be within the spirit and scope of the present invention.

In a receive step 120, processor 40 receives, from probe 22, a given mapping point 90B comprising a location in heart 26 and electroanatomical data for the location. In an increment step 122, processor 40 increments the counter, and using embodiments described hereinabove, the processor calculates a point error value for the mapping point in a first calculation step 124. In some embodiments, processor 40 can increment the counter by 1 for each mapping point 90B received. In alternative embodiments, upon receiving a given mapping point 90B, processor 40 can increment the counter by storing a value indicating the time elapsed since performing the most recent registration.

In a first comparison step 126, if the point error value calculated for the received mapping point is less than the specified point error threshold, then processor 40 includes the given mapping point in map 48 in an inclusion step 128. On the other hand, if the point error value calculated for the received mapping point is greater than or equal to the point error threshold, then processor 40 excludes the given mapping point from map 48 in an exclusion step 130.

In a second comparison step 132, if the value stored in the counter is greater than or equal to a specific counter threshold (e.g., a specific number of mapping points or a specific time period elapsing since the previous registration), then processor 40 resets the counter in a reset step 134, and in a registration step 136 performs a tentative registration between mapping points all received mapping points 90 and image 92. In a second calculation step 138, processor 40 uses the tentative registration to calculate a respective tentative point error value for each mapping point 90A and 90B, and calculates a tentative cumulative error value for the all the received mapping points. Each of the tentative point mapping values indicates a quality of its respective mapping point relative to the tentative registration, and the tentative cumulative point error value indicates an overall quality of the tentative registration.

In a third comparison step 140, if the tentative cumulative error value is less than the (current) cumulative error value, then in an acceptance step 142, processor 40 accepts the tentative registration, the tentative point values and the tentative cumulative error value. To accept the tentative registration, processor 40 replaces the current registration with the tentative registration, to accept the tentative point values, the processor replaces the current point error values with the corresponding tentative point error values, and to accept the tentative cumulative error value, the processor replaces the current cumulative error value with the tentative cumulative error value.

Finally, in a remapping step 144, processor 40 replaces map 48 with a new map comprising electroanatomical data for the mapping points whose updated point error values are less than the update cumulative error value, and the method continues with step 120. Returning to step 140, if the tentative cumulative error value is greater than the point error threshold, then the method continues with step 120. Returning to step 132, if the value in the counter is less than the specified counter threshold, then the method also continues with step 120.

In embodiments herein, the initial mapping points in step 64 may also be referred to herein as a first set of mapping points 90, the initial registration performed in step 66 may also be referred to as a first registration, and the point error values calculated in steps 68 and 124 may also be referred to as first point error values, and the cumulative error values calculated in step 68 may also be referred to herein as a first point error value and a first cumulative error value, respectively. Likewise, the mapping points collected in step 120 (i.e., until the condition in step 132 is met) may also be referred to herein as a second set of mapping points 90, the tentative registration performed in step 136 may also be referred to herein as a second registration, and the tentative point error and tentative cumulative error values calculated in step 138 may also be referred to herein as a second point error value and a second cumulative error value, respectively.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
   acquiring, from an imaging system, an image of a body cavity;

receiving first and second sets of mapping points from a probe having a location sensor and inserted into the body cavity;

performing, by a processor, a first registration between the mapping points in the first set and the image, each of the mapping points in the first set having a respective first point error value, the first registration having a first cumulative error value indicating a quality of the first registration;

generating, using the first registration, a three-dimensional (3D) anatomical map comprising the mapping points in the first set whose respective first point error values are less than a point error threshold;

performing a second registration between the mapping points in the first and the second sets and the image, each of the mapping points in the first and the second sets having a respective second point error value, the second registration having a second cumulative error value lower than the first cumulative error value; and generating an updated 3D anatomical map comprising the mapping points in the first and the second sets whose respective second point error values are less than the point error threshold.

2. The method according to claim 1, and comprising presenting the 3D anatomical map and the updated 3D anatomical map on a display.

3. The method according to claim 1, wherein the body cavity comprises a heart, and wherein the probe comprises an intracardiac catheter.

4. The method according to claim 1, wherein the 3D anatomical map comprises an electroanatomical map.

5. The method according to claim 1, wherein the second registration is performed upon a specific time period elapsing after the first registration.

6. The method according to claim 1, wherein the second registration is performed upon the second set having a specific number of mapping points.

7. The method according to claim 1, and comprising, prior to performing the first registration, specifying the point error threshold.

8. The method according to claim 1, wherein the first point error value for a given mapping point indicates a first quality of the given mapping point relative to the first registration, and wherein the second point error value for the given mapping point indicates a second quality of the given mapping point relative to the second registration.

9. The method according to claim 8, and comprising prior to the second registration, calculating a respective first point error value for each of the mapping points in the second set, and including, in the first map, the mapping points in the second set whose respective first point error values are less than the point error threshold.

10. An apparatus, comprising:
a probe, configured for insertion into a body cavity of a patient and comprising a location sensor for measuring a position of a distal end of the probe inside the body cavity; and
a processor configured:
to acquire, from an imaging system, an image of the body cavity,
to receive first and second sets of mapping points from the probe inserted into the body cavity,
to perform a first registration between the mapping points in the first set and the image, each of the mapping points in the first set having a respective first point error value, the first registration having a first cumulative error value indicating a quality of the first registration,
to generate, using the first registration, a three-dimensional (3D) anatomical map comprising the mapping points in the first set whose respective first point error values are less than a point error threshold,
to perform a second registration between the mapping points in the first and the second sets and the image, each of the mapping points in the first and the second sets having a respective second point error value, the second registration having a second cumulative error value lower than the first cumulative error value, and
to generate an updated 3D anatomical map comprising the mapping points in the first and the second sets whose respective second point error values are less than the point error threshold.

11. The apparatus according to claim 10, and comprising a display, and wherein the processor is configured to present the 3D anatomical map and the updated 3D anatomical map on a display.

12. The apparatus according to claim 10, wherein the body cavity comprises a heart, and wherein the probe comprises an intracardiac catheter.

13. The apparatus according to claim 10, wherein the 3D anatomical map comprises an electroanatomical map.

14. The apparatus according to claim 10, wherein the processor is configured to perform the second registration upon a specific time period elapsing after the first registration.

15. The apparatus according to claim 10, wherein the processor is configured to perform the second registration upon the second set having a specific number of mapping points.

16. The apparatus according to claim 10, wherein the processor is configured, prior to performing the first registration, to specify the point error threshold.

17. The apparatus according to claim 10, wherein the first point error value for a given mapping point indicates a first quality of the given mapping point relative to the first registration, and wherein the second point error value for the given mapping point indicates a second quality of the given mapping point relative to the second registration.

18. The apparatus according to claim 17, wherein the processor is configured, prior to the second registration, to calculate a respective first point error value for each of the mapping points in the second set, and to include, in the first map, the mapping points in the second set whose respective first point error values are less than the point error threshold.

19. A computer software product, operated in conjunction with a probe that is configured for insertion into a body cavity of a patient and includes a location sensor for measuring a location of a distal end of the probe inside the body cavity, the product comprising a non-transitory computer-readable medium, in which program instructions are stored, which instructions, when read by a computer, cause the computer:
to acquire, from an imaging system, an image of the body cavity,
to receive first and second sets of mapping points from a probe inserted into the body cavity,
to perform a first registration between the mapping points in the first set and the image, each of the mapping points in the first set having a respective first point error value, the first registration having a first cumulative error value indicating a quality of the first registration, to generate, using the first registration, a three-dimensional (3D) anatomical map comprising the mapping points in the first set whose respective first point error values are less than a point error threshold, to perform a second registration between the mapping points in the first and the second sets and the image, each of the mapping points in the first and the second sets having a respective second point error value, the second registration having a second cumulative error value lower than the first cumulative error value, and to generate an updated 3D anatomical map comprising the mapping points in the first and the second sets whose respective second point error values are less than the point error threshold.

* * * * *